US009232919B1

(12) United States Patent
Asfora (10) Patent No.: US 9,232,919 B1
(45) Date of Patent: Jan. 12, 2016

(54) CRANIOSYNOSTOSIS DETECTION SYSTEM

(75) Inventor: Wilson T. Asfora, Sioux Falls, SD (US)

(73) Assignee: Asfora IP, LLC, Sioux Falls, SD (US)

( * ) Notice: Subject to any disclaimer, the term of this patent is extended or adjusted under 35 U.S.C. 154(b) by 368 days.

(21) Appl. No.: 12/069,390

(22) Filed: Feb. 11, 2008

(51) Int. Cl.
*A61B 5/103* (2006.01)
*A61B 5/00* (2006.01)
*A61B 5/11* (2006.01)
*A61B 5/113* (2006.01)

(52) U.S. Cl.
CPC .............. *A61B 5/4504* (2013.01); *A61B 5/11* (2013.01); *A61B 5/113* (2013.01); *A61B 2503/04* (2013.01); *A61B 2503/045* (2013.01)

(58) Field of Classification Search
CPC ........ A61B 5/11; A61B 5/113; A61B 5/4504; A61B 2503/04; A61B 2503/045
USPC .......................................................... 600/587
See application file for complete search history.

(56) References Cited

U.S. PATENT DOCUMENTS

| 4,600,013 | A | | 7/1986 | Landy et al. | |
|---|---|---|---|---|---|
| 4,860,766 | A | * | 8/1989 | Sackner | 600/587 |
| 5,630,422 | A | * | 5/1997 | Zanakis | 600/595 |
| 7,435,232 | B2 | * | 10/2008 | Liebschner | 600/587 |
| 2004/0175685 | A1 | * | 9/2004 | Sze et al. | 434/270 |
| 2008/0223119 | A1 | * | 9/2008 | Phan et al. | 73/105 |

OTHER PUBLICATIONS

Jeremy J. Mao, DDS, MSD, PhD, et al; "Biomechanics of Craniofacial Sutures: Orthopedic Implications", Angle Orthodontist, pp. 128-135, vol. 73, No. 2, 2003.
Molly J. Markey et al., "In vivo cranial suture function and suture morphology . . . ", The Journal of Experimental Biology 209, Apr. 11, 2006, pp. 2085-2102.
J.J. Mao, "Mechanobiology of Craniofacial Sutures", J Dent Res 81 (12), pp. 810-816, 2002.
Gregory J.A. Murad, MD, et al., "Endoscopic-assisted repair of craniosynostosis", Neurosurg Focus, vol. 19, pp. 1-10, Dec. 2005.
"Research: The Inherent Rhythmic Motion of the Cranial Bones", The Cranial Academy, Inc., 2005, http://www.cranialacademy.org/research6.html.

* cited by examiner

*Primary Examiner* — Lee S Cohen
*Assistant Examiner* — Emily Lloyd
(74) *Attorney, Agent, or Firm* — Jeffrey A. Proehl; Woods, Fuller, Shultz & Smith, P.C.

(57) ABSTRACT

A craniosynostosis detection system is disclosed that may comprise a movement detection apparatus configured to detect movement in a surface of the scalp of the patient along areas between bones of the skull when at least a portion of the movement detection apparatus is positioned adjacent to the surface of the scalp. The movement detection apparatus may generate a signal corresponding to movement detected by the movement detection apparatus. A signal processing apparatus may be operatively connected to the movement detection apparatus and configured to receive the movement signal from the movement detection apparatus. A data display apparatus may be operatively connected to the signal processing apparatus and configured to display a representation of movement detected by the movement detection apparatus. The absence of movement of the scalp over the sutures, which correspond to the brain pulsations, is diagnostic of craniosynostosis.

18 Claims, 10 Drawing Sheets

CRANIOSYNOSTOSIS DETECTION SYSTEM

BACKGROUND

1. Field

The present invention relates to the early detection of craniosynostosis in neonates and infants, utilizing a simple, noninvasive and very rapid diagnostic method without the use of x-ray technology, and even before any skull deformity is noticeable.

2. Description of the Prior Art

For a period of time after birth, the sutures between the flat bones of the skull of an infant remain open and unfused to permit brain and skull growth. The flat bones are separated by areas of dense connective tissue which are fibrous and moveable which are needed for the ongoing growth. The areas of connective tissue are eventually ossified into bone. However, while the posterior areas of connective tissue between the bones may close by eight weeks after birth, the anterior rears of connective tissue may remain up to eighteen months after birth before the ossification occurs. Thus, the time periods for such ossification may vary greatly.

Craniosynostosis is a condition in which the sutures between the flat bones of the skull of the infant or young child are closed or close prematurely. The premature closure of the sutures in craniosynostosis may result in increased intracranial pressure and skull deformity, which may have a detrimental effect on the development of an infant's brain as the brain is unnaturally constricted. Only one in a thousand infants will be diagnosed with the defect, so awareness of the condition is not high.

Unfortunately, the craniosynostosis condition is often not detected until after the sutures of the skull bones have fully fused and there is an obvious skull deformity. The remedies for the condition at this point are more complicated. The condition may be detected by a noticeable abnormality in the shape of the infant's head. However, this is not a reliable indicator because even if there is a noticeable change in the shape of the infant's head, the misshapen head may simply be the result of the effects of labor and delivery on the soft unfused skull, or exposure of the unfused skull to long periods of pressure applied to the infant's head while lying in the same position; the so-called plagiocephaly.

Moreover, there are few if any simple and reliable ways of diagnosing the early craniosynostosis condition before significant skull deformity, or discriminating between it and the less serious positional plagiocephaly, particularly in the clinical setting. Methods of detection such as CT scan, x-ray, ultra sound or magnetic resonance imaging procedures may be effective at detecting the condition at an early stage, but are rarely performed as a matter of course in the normal "checkup" examination of the infant unless the condition is severe enough to be noticed. Also, in the early stages in which the suture is partially open or fused at a very small segment, false negatives are high. As the treatment of craniosynostosis involves significant skull reconstruction, it is desirable to have a means of detecting craniosynostosis that is relatively accurate, especially at the early stages of the condition, for better surgical results and to minimize the surgical intervention using a less invasive procedure. Detecting and treating craniosynostosis as soon as possible after the initial onset of cranial bone fusion is also desirable to minimize any negative effects on the normal growth and development of the child's brain.

What is needed therefore is a system for detecting premature fusion of cranial bones as close as possible to the first onset of the premature fusion of the sutures, while being simple and noninvasive so that it may be performed as a part of the normal medical check ups provided to newborn and infant children.

SUMMARY

In view of the foregoing disadvantages inherent in the known types of methods and means of detection of craniosynostosis now present in the prior art, the present disclosure describes a new craniosynostosis detection system which may be utilized for detecting the symptoms of craniosynostosis to facilitate the diagnosis of craniosynostosis in a simple and noninvasive manner.

The brain pulsates with each heartbeat and this pulsation is transmitted to the skull bones which also pulsate. The present disclosure relates to a craniosynostosis detection system that may comprise a movement detection apparatus configured to detect movement in the surface of the scalp 3 of the patient along areas between bones of the skull when at least a portion of the movement detection apparatus is positioned adjacent to the surface of the scalp. The movement detection apparatus may generate a signal corresponding to movement detected by the movement detection apparatus. A signal processing apparatus may be operatively connected to the movement detection apparatus and configured to receive the movement signal from the movement detection apparatus. A data display apparatus may be operatively connected to the signal processing apparatus and configured to display a representation of movement detected by the movement detection apparatus. Thus, in a normal infant, the recording of brain pulse waves from the scalp 3 is possible due to movement (lack of stress) of the unfused normal skull bones.

There has thus been outlined, rather broadly, some of the more important elements of the invention in order that the detailed description thereof that follows may be better understood, and in order that the present contribution to the art may be better appreciated. There are additional elements of the invention that will be described hereinafter and which will form the subject matter of the claims appended hereto.

In this respect, before explaining at least one embodiment or implementation in greater detail, it is to be understood that the scope of the invention is not limited in its application to the details of construction and to the arrangements of the components set forth in the following description or illustrated in the drawings. The invention is capable of other embodiments and implementations and is thus capable of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present disclosure. It is important, therefore, that the claims be regarded as including such equivalent constructions insofar as they do not depart from the spirit and scope of the present invention.

The advantages of the various embodiments of the present invention, along with the various features of novelty that characterize the invention, are disclosed in the following descriptive matter and accompanying drawings.

BRIEF DESCRIPTION OF THE DRAWINGS

The disclosure will be better understood when consideration is given to the drawings and the detailed description which follows. Such description makes reference to the annexed drawings wherein.

DETAILED DESCRIPTION

With reference now to the drawings, and in particular to FIGS. 1 through 10 thereof, a new craniosynostosis detection system embodying the principles and concepts of the disclosed subject matter will be described.

Figure 3:
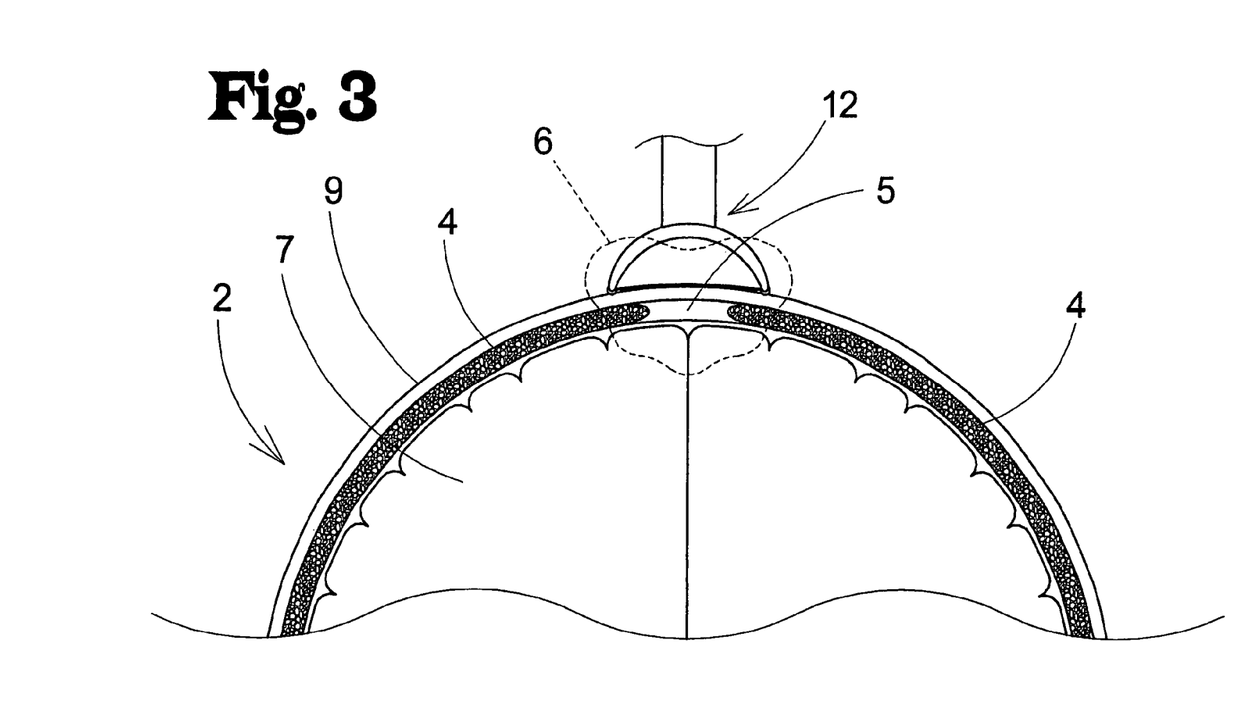
FIG. 3 is a schematic sectional view of the movement detection apparatus of the system according to an illustrative embodiment, shown in relation to a sectional view of the skull of a patient.
Figure 4:
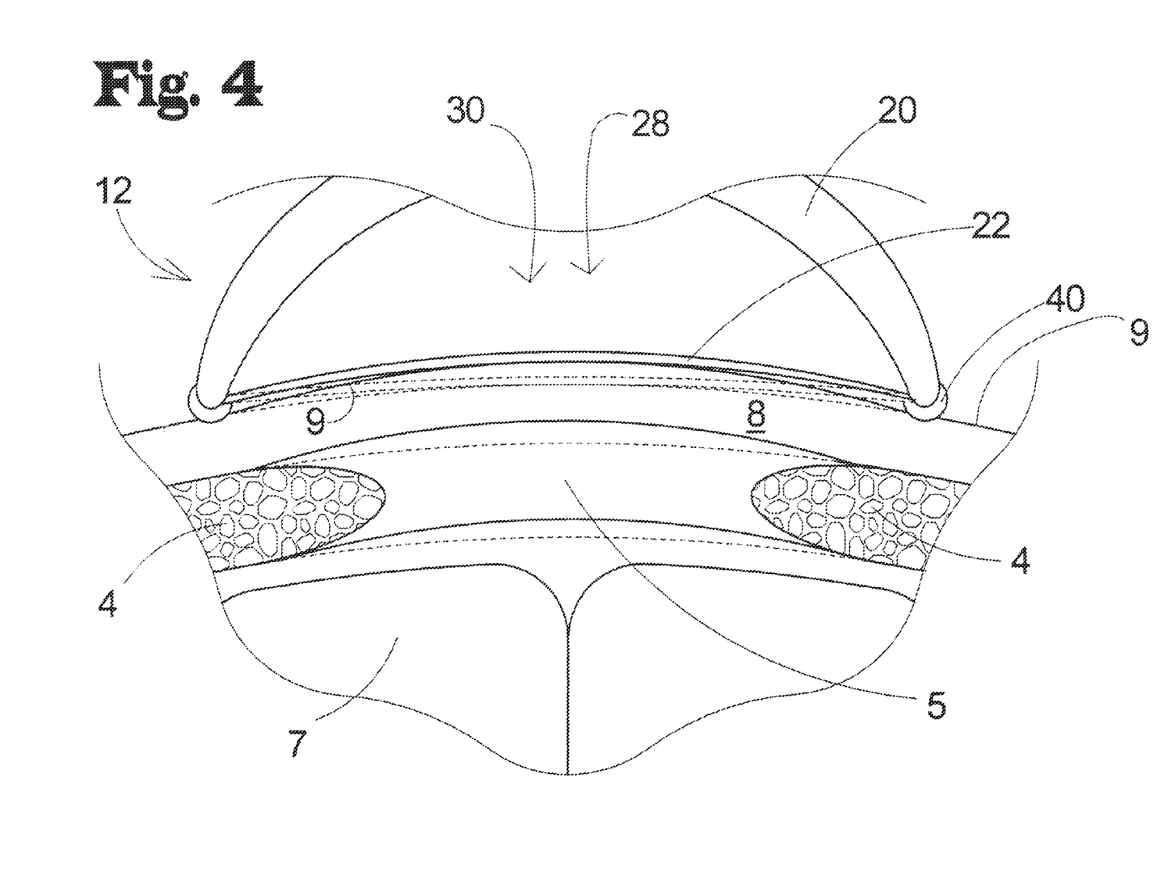
FIG. 4 is a schematic enlarged sectional view of the showing of FIG. 3.

As a matter of background and clarity for the following description, and referring to FIGS. 3 and 4, the head 1 of the infant patient has a skull 2 formed of a plurality of relatively flat bones 4 with sutures 5 therebetween. The sutures 5 are characterized by gaps in which fibrous connective tissue 6 is located and joins the spaced bones 4. The fibrous connective tissue 6 extends along the sutures 5 between the bones 4. The brain 7 of the patient is located on the skull 2. The scalp 8 of the patient's head overlies the bones 4 of the skull 2 as well as the fibrous connective tissue 6 in the sutures 5. The scalp 8 has an outer surface 9, and the patient may have hair extending from the outer surface 9.

The craniosynostosis detection system 10 may comprise a number of elements, including a movement detection apparatus 12 configured to detect movement in scalp of a patient along the sutures of the skull, a signal processing apparatus 14 configured to receive the movement signal from the movement detection apparatus 12, and a data display apparatus 16 configured to display a representation of the movement detected by the movement detection apparatus 12 and represented by the movement signal. In some embodiments, the system 10 may also include a data recordation apparatus 18 configured to record a representation of the movement detected by the movement detection apparatus 12 and represented by the movement signal.

The craniosynostosis detection system 10 of the disclosure is directed to detecting the symptoms of the craniosynostosis condition in a patient at the earliest stages of the condition. It has been observed that the head 1 of a patient having sutures 5 of normal character with areas of fibrous connective tissue 6 between the bones 4 will exhibit relatively minute expansions and relaxations of the areas of the scalp 8 over the sutures 5, which results in movement of the outer surface 9 of the scalp 8 over the sutures during a period of time. These scalp expansions and relaxations are caused by blood pulsing through the brain 7 of the patient as a result of the heartbeat, and the resulting movement of the outer surface 9 of the scalp is generally not perceptible to the eye of the caregiver or physician, but are nonetheless detectible. One manner of detecting the possibility of craniosynostosis is to observe the behavior of the outer surface 9 of the scalp 8 over the sutures 5 to determine if these expansions and relaxations of the scalp are occurring. If these movements of the scalp surface 9 are not detected, or are present in some areas but not in other areas, performing further testing to determine if the craniosynostosis condition is present may be employed. However, if movement of the scalp surface 9 is detected, then a determination may be made that the craniosynostosis condition likely does not exist. It will be recognized that the degree of movement displayed by the outer scalp surface 9 may correspond to the degree to which the sutures 5 of the scalp have ossified and the fibrous connective tissue 6 is no longer present, and therefore the movement signal may not provide an absolute indicator of fusion of the bones 4 but may provide a relative indicator that may be interpreted by the user or by interpretive algorithms incorporated into software or firmware. Comparison may also be made between different sutures.

The movement detection apparatus 12 of the craniosynostosis detection system 10 may be employed to detect the movement (or the lack thereof) of the scalp 8 that provides an indication to the user of the system 10 whether the craniosynostosis condition is present in the patient. In general, the movement detection apparatus 12 generates a movement signal corresponding to movement (if any) detected by the movement detection apparatus when the movement detection apparatus is brought into contact with the outer surface 9 of the scalp 8 of the patient.

The movement detection apparatus 12 is primarily directed to detecting small movements of the scalp 8 of the patient when the detection apparatus 12 is positioned on or against the outer surface 9 of the scalp at a location above one of more of the sutures 5 of the skull 2 of the patient. The movement detection apparatus 12 may be of a size and shape that may be easily held in the hand of the user so that the user is able to hold the detection apparatus 12 against the scalp 8 of the patient. Preferably the movement detection apparatus 12 may be held in one hand of the user, allowing the other hand of the user to be free to perform other actions, such as cradling the head 1 of the patient to hold the head still.

As an illustration of the foregoing, FIGS. 3 and 4 of the drawings illustrate the positioning of the movement detection apparatus 12 on the scalp 8 of the patient above the sagittal suture 5 located between the left and right parietal bones 4 of the skull 2. For example, tests for any movements of the surface 9 of the scalp 8 may be taken along the length of the sagittal suture between the parietal bones. The tests or readings may also be taken along the coronal suture between the frontal and parietal bones, along the metopic suture between the left and right sections of the frontal bone and along the lambdoid suture between the occipital and the two parietal bones, at the anterior fontanelle at the junction of the sagittal and coronal sutures and at the posterior fontanelle at the junction of the sagittal and lambdoid sutures. FIGS. 3 and 4 depict cranial bones that have not gone through synostosis, or the fusion of ossified bones, to form a rigid bone to bone connection, and a fibrous joint of soft membranous tissue is located between the sections of ossified cranial bones.

FIG. 4 is a magnification of a section of FIG. 3, and illustrates the contact area between the support 20 and the membrane 22 of the movement detection apparatus 12 and the surface 9 of the scalp 8 of the head 1 of the patient. In FIG. 4, the projection or expansion of the scalp 8 and tissue 6 of the cranial fibrous joint during the pulse of blood through the brain 7 and surrounding structures is shown in solid lines, and the unprojected or relaxed boundary of the scalp 8 and tissue 6 of the joint between pulses of blood through the brain 7 is shown in broken lines. The slight protrusion or expansion of the outer surface 9 of the scalp 8 during the pulse of blood through the brain 7 may be detectable when a fibrous joint exists between the ossified cranial bones. If the cranial bones 4 are fused together at the suture, then little or no protrusion of the outer surface 9 of the scalp 8 is detectable.

In greater detail, the movement detection apparatus 12 may generally comprise a support 20 for positioning adjacent to or against the scalp 8 of the patient, a membrane 22 mounted on the support 20 for positioning against outer surface 9 of the scalp of the patient such that a portion of the membrane is able to move with the scalp, and a movement detector 24 configured to detect movement of the membrane with respect to the support.

The support 20 may be configured to be positioned adjacent to, and in various embodiments against, the scalp of the patient during use of the craniosynostosis detection system 10. The support 20 may include spaced support portions 26, 27 which define a gap 28 therebetween. During use of the system 10, the gap 28 may be positioned over and above the location of a suture 5 of the skull of the patient's head, and the support portions 26, 27 may be positioned against the scalp 8 at locations spaced from the suture 5. The support portions 26, 27 may be placed against locations on the scalp 8 that are believed to be over bones 4 of the skull, and thus are not likely to move to the degree that the areas above a suture 5 with fibrous connective tissue will move. Thus, the spacing between the support portions 26, 27 and the width of the gap 28 should be suitable for permitting the support portions to simultaneously contact locations on the scalp of the patient above the bones 4 of the skull while the gap 28 is located above the suture 5. The support 20 may include a first support portion 26 and a second support portion 27 that define the gap 28 therebetween. The support portions 26, 27 may also form mounting points or locations for the membrane 22. The support 20 may be substantially rigid or inflexible in character so that the membrane 22 is not affected by any flexing of the support 20.

In various embodiments, the support 20 may define a cavity 30 which is brought up adjacent to the scalp 8 of the patient during use of the system 10. The gap 28 may be located across an opening 32 of the cavity 30, and the cavity may provide a space for movement of the membrane 22 with respect to the support 20. The support 20 may define a surface 34 that is concave in shape, and in some embodiments the concave surface is a semispherical surface (see FIG. 5), and in some embodiments the concave surface is a semi-cylindrical surface (see FIG. 6).

In some embodiments, the support 20 may have a structure similar to the bell sleeve of a stethoscope, and provides a generally circular perimeter on which the membrane 22 is mounted. In such embodiments, the movement detection apparatus 12 may be similar in function to the pickup of a stethoscope and the membrane 22 may be analogous in function to the diaphragm of the stethoscope.

Optionally, the system 10 may have a structure that includes a plurality of the supports 20 that, for example, hold a plurality of the membranes 22 in a linear array for positioning along the generally linear suture of the skull.

When the support 20 is abutted against the head of the patient, the membrane 22 of the craniosynostosis detection system 10 is positioned against and contacts the surface 9 of the scalp 8 (or the hair overlying the scalp) of the patient such that the membrane 22 moves with the scalp 8 as the scalp experiences the expansions and relaxations caused by the blood pulsing through the brain 7 of the patient. The membrane 22 extends across the gap 28 defined by the support 20. The membrane 22 may be flexible in character to facilitate the conforming of the membrane to the surface 9 of the scalp, as the scalp may not be (and is unlikely to be) completely flat between the positions of the support portions 26, 27 and likely will have some degree of curvature. Contact of the membrane 22 with the curvature of the scalp 8 may cause some movement of the membrane 22 that needs to be accounted for during the observation of the output of the system 10, but the user is looking for changes caused by the movement of the surface 9 of the scalp, which will tend to increase and decrease in a somewhat regular manner, and any initial movement caused by the initial contact may be noted by the user and disregarded. Further, the flexibility of the membrane 22 may facilitate free movement of the membrane 22 with the scalp surface 9. The membrane 22 may also be stretchable to a degree to facilitate movement of the membrane 22 with the scalp. To provide one or more of these characteristics, the membrane 22 may be formed of an elastomeric material. In some configurations, the membrane 22 may close the opening of the support. The membrane 22 may have an outward surface 36 that is positionable in contact with the outer surface 9 of the scalp 8, and may also have an inward surface 38 that faces at least a portion of the support 20.

In some embodiments, the membrane 22 may be mounted on the support 20 by a connector structure 40 that connects the membrane to the support. The connector may be located along at least a portion of the perimeter of the membrane, and may secure the membrane to the support portions. Optionally, more than one membrane 22 may be employed on the same support 20, with each membrane having at least one movement detecting apparatus 12. The connector structure 40 may' project beyond the plane of the outward surface 36 of the membrane 22, or may be coplanar with the plane of the exterior surface of the membrane.

The movement detector 24 of the movement detection apparatus 12 is configured to detect movement of the membrane 22. In some embodiments, the movement detector 24 is configured to detect movement of the membrane 22 with respect to the support 20, although this is not a critical function. Thus, movement of the membrane 22 by the outer surface 9 of the scalp 8 when the membrane is positioned in contact with the surface 9 may be detected. The movement detector 24 may generate a movement signal which corresponds to and varies with the degree or extent of movement of the membrane 22 detected by the detector 24. In some embodiments, the movement detector 24 may be mounted on the support 20 to detect movement of the membrane 22 with respect to the support. In other embodiments, the movement detector 24 may be mounted on (or formed as a part of) the membrane 22 to detect movement of the membrane. In some implementations, more than one movement detector may be employed on one or more membranes 22.

In various embodiments, the movement detector 24 detects movement of the membrane 22 through the detection of changes in strain in the membrane. The strain, or the change in strain, in the membrane 22 may be detected or measured using any suitable strain detecting device 42. In some implementations, the strain detecting device 42 is employed either alone or in combination with a Wheatstone bridge 44. The strain detecting device 42 may be mounted on the membrane 22 is any suitable manner, including but not limited to being mounted on the inward surface 38 of the membrane, or being integrated into or within the membrane, or being sandwiched between layers of material forming the membrane.

Figure 5:
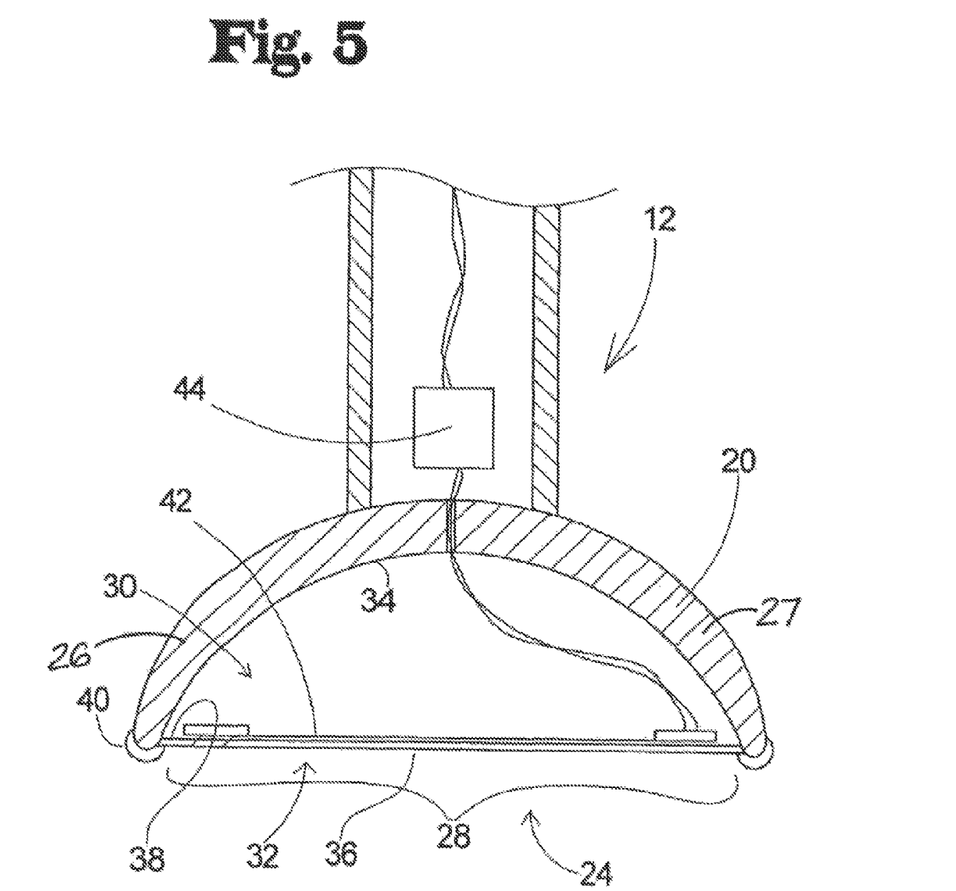
FIG. 5 is a schematic sectional view of the detection system, according to one illustrative embodiment.
Figure 6:
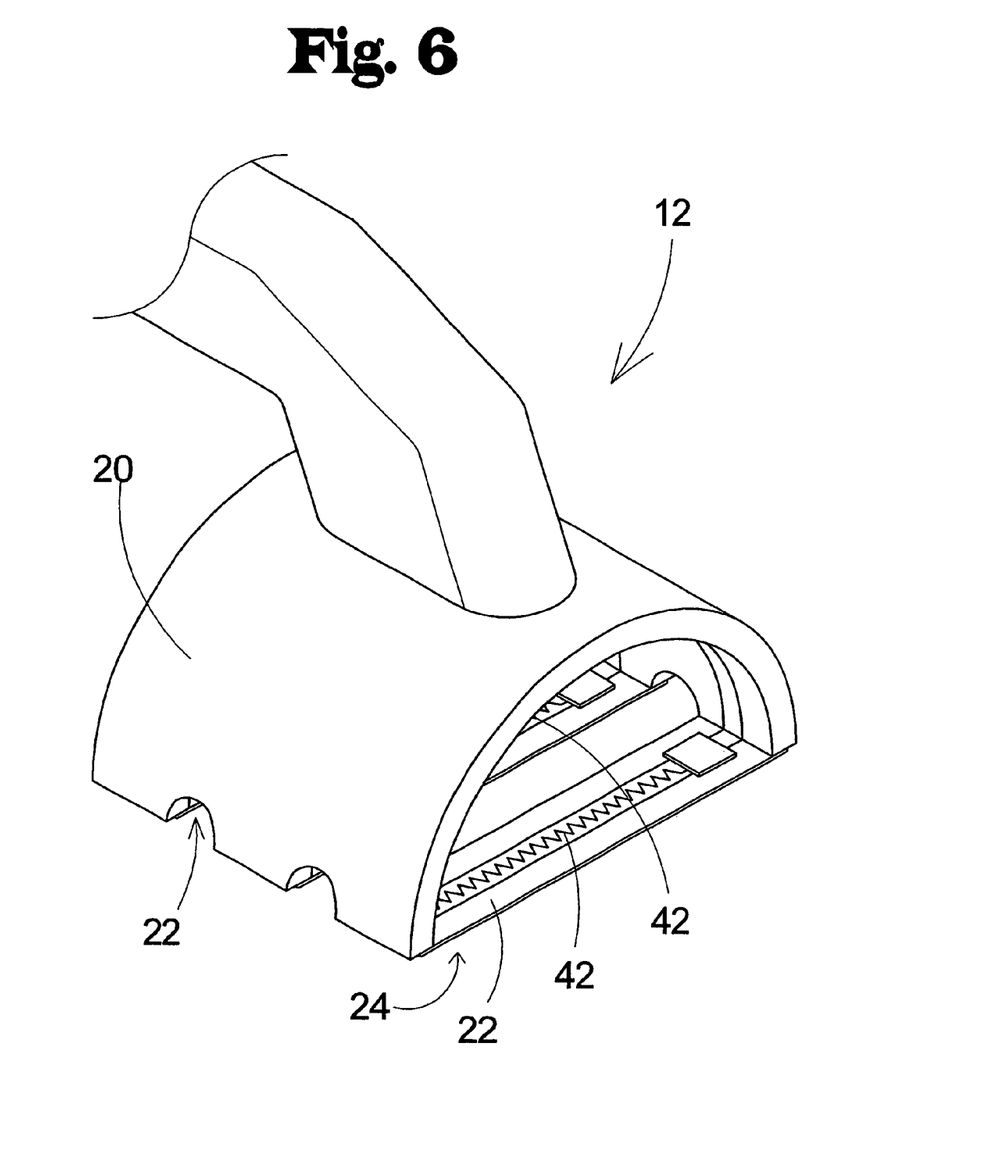
FIG. 6 is a schematic perspective view of the detection system, according to another illustrative embodiment.

In some embodiments, the strain detecting device 42 of the movement detector 24 may comprise a foil strain gauge 42 employed in combination with a Wheatstone bridge 44 if required (see FIG. 5). Conductors may provide electrical communication between the foil strain gauge and the Wheatstone bridge. Variations of the configuration of the arrangement shown in FIG. 7 will be evident to those of skill in the art. While the Wheatstone bridge 44 is depicted as being located outside of the support 20, the location of the Wheatstone bridge may be virtually anywhere, even on the membrane 22.

Figure 7:
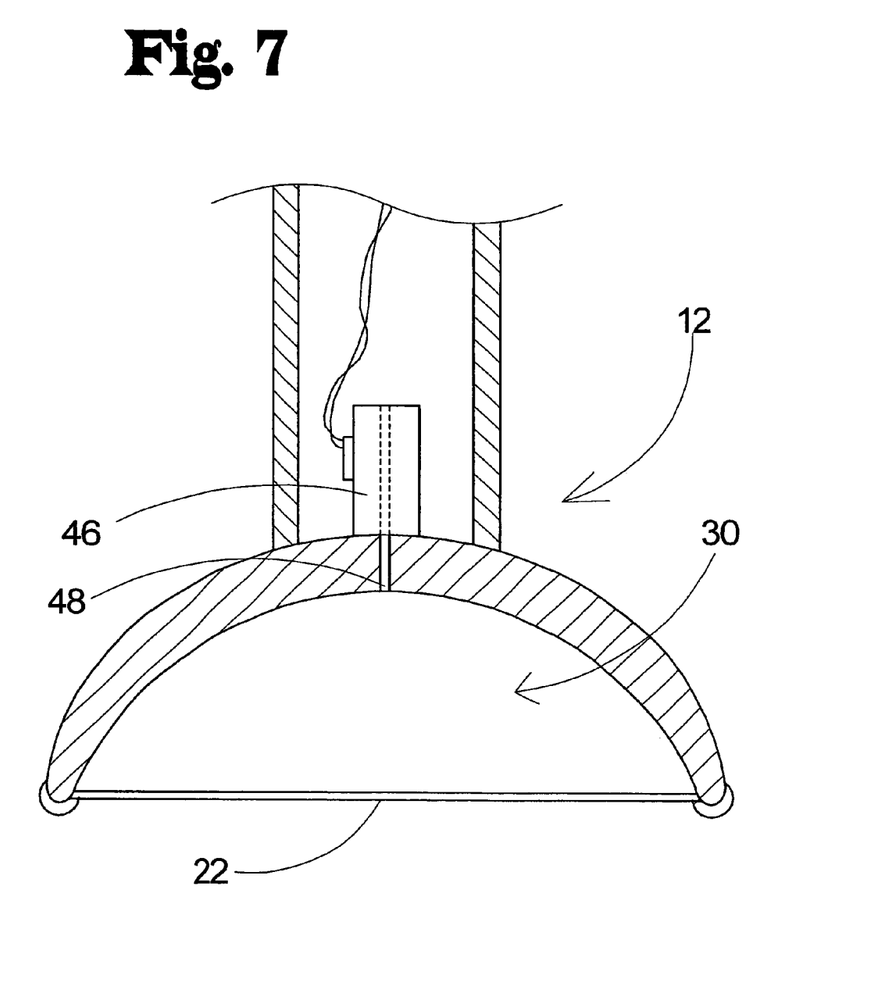
FIG. 7 is a schematic sectional view of the detection system, according to another illustrative embodiment.
Figure 8:
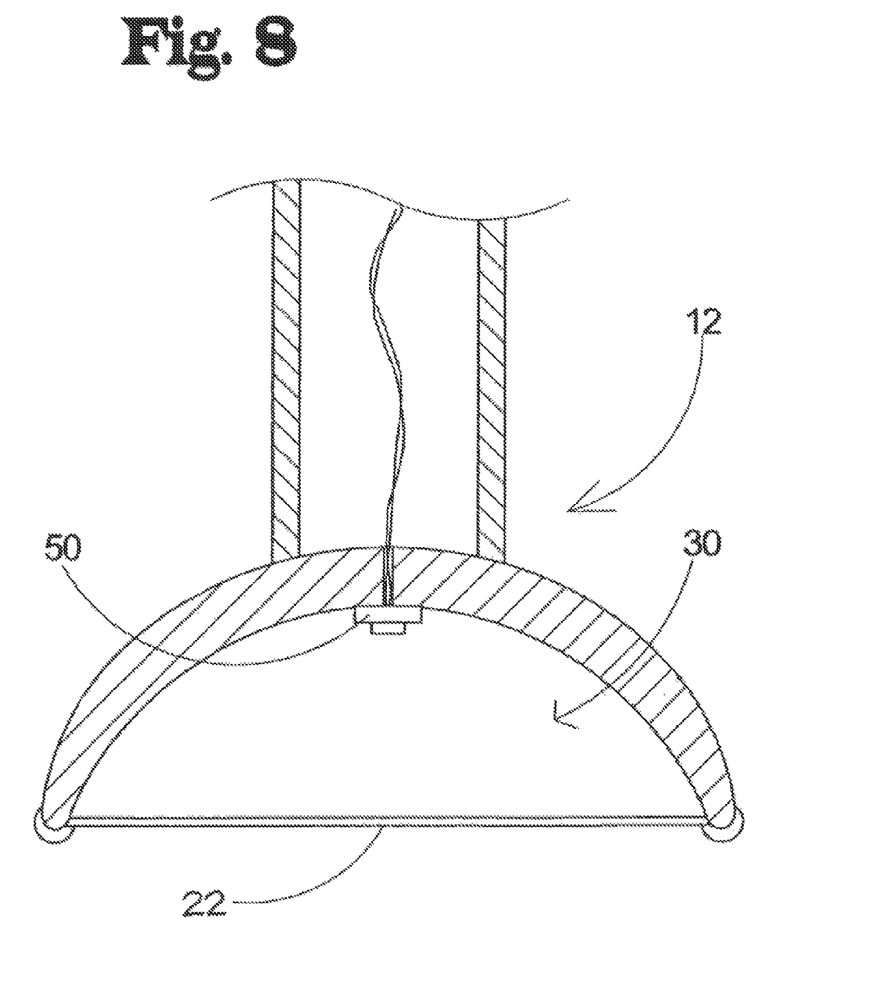
FIG. 8 is a schematic sectional view of the detection system, according to another illustrative embodiment.

In other embodiments of the system 10, the movement detector 24 may employ other technologies or techniques for detecting movement of the membrane 22. For example, the movement detector 24 may comprise an air flow sensor 46 for detecting the flow (or non-flow) of air into and out of the cavity 30 formed by the support 20 and the membrane 22. FIG. 7 shows an embodiment in which the membrane 22 is substantially sealed to the support 20 at the support portions 26, 27, and the only open air access to the cavity 30 is through a vent 48. In these embodiments, the expansion of the scalp 8 above the fibrous joint area of an un-fused cranial suture 5 pushes against the membrane 22 which in turn forces air out of the cavity 30 through the vent 48. The air flow sensor 46 is positioned in fluid communication with the vent 48 in a manner that permits the air flow sensor to detect the passage of air out of and back into the cavity 30. The amount or mass of air moved out of the cavity 30 and through the vent 48 generally corresponds to the degree of the expansion (if any) of the surface 9 of the scalp 8.

In further embodiments, the movement detector 24 may be configured to detect small changes in pressure inside a substantially sealed cavity, such as the cavity 30 formed by the support 20 and the membrane 22. The movement detector 24 may comprise a pressure transducer 50 to detect changes or variations in pressure of the gas (for example, air) in the cavity 30 in response to the deformation of the membrane 22 by the surface 9 of the scalp 8 over the fibrous tissue 6 (see FIG. 8). In these embodiments, there is no passage for the gas in the cavity 30 to be released from the cavity 30 when the membrane 22 is deformed inwardly by movement of the scalp 8, which thus causes an increase in the pressure of the gas that is detected by the pressure transducer 50 located in, or in communication with, the cavity.

Figure 9:
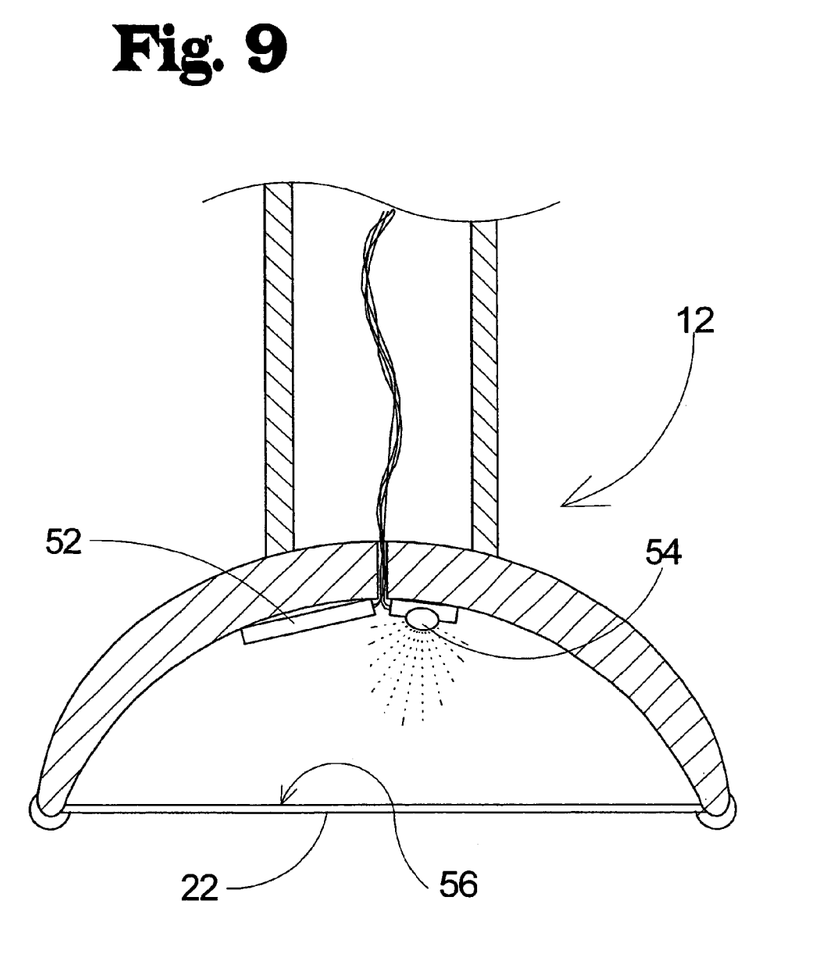
FIG. 9 is a schematic sectional view of the detection system, according to another illustrative embodiment.
Figure 10:
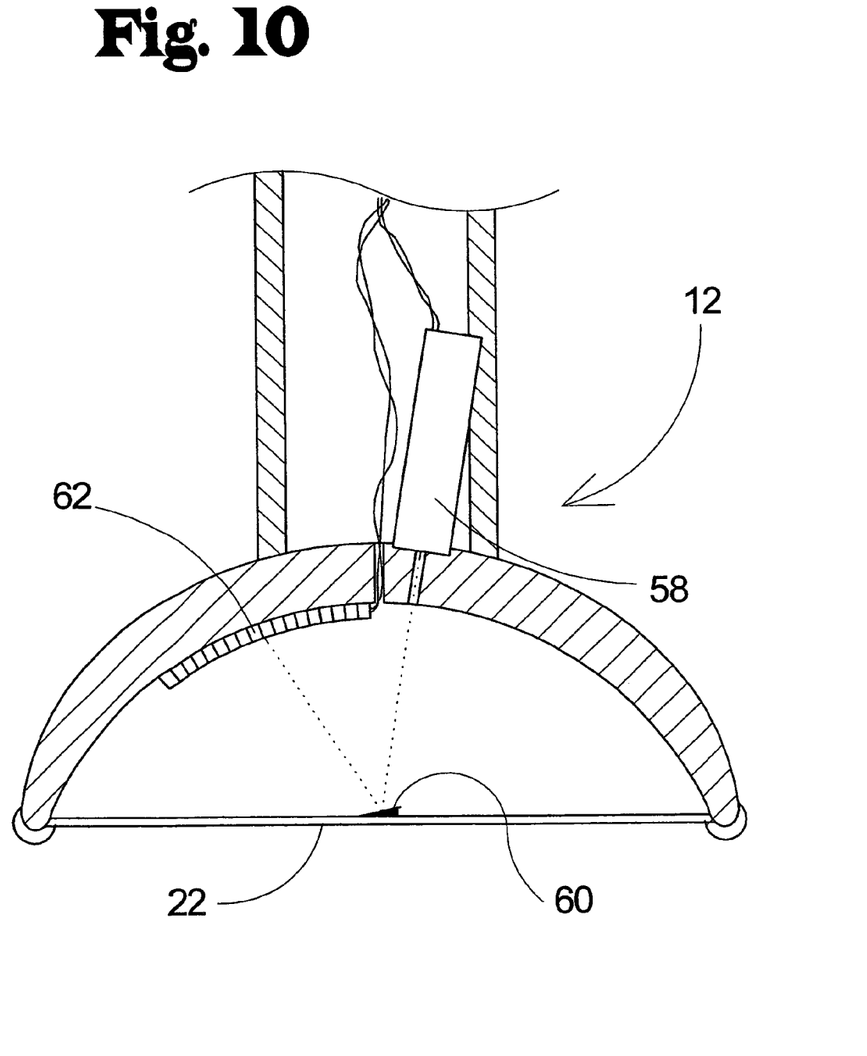
FIG. 10 is a schematic sectional view of the detection system, according to another illustrative embodiment.

In still other embodiments, the movement detector 24 may employ optical means for detecting movement of the membrane 22. For example, the detector 24 may include an optical sensor 52 (such as is depicted in FIG. 9). The optical sensor 52 may be employed in combination with a light source 54 that may be mounted on the support 20, and a patterned surface 56 may be employed on the inward side or surface 38 of the membrane 22. The light source 54 may be positioned so as to illuminate the patterned surface 56. The optical sensor 52 may periodically capture an image of a portion of the patterned surface 56 on the membrane 22 as graphic signals and transmit the signals to a digital signal processor that detects patterns in the images and determines if and how much the captured portion of the pattern has moved since a previous image was captured. Based on the change in the portion of the pattern captured over a sequence or series of images, or lack of any substantial change, the digital signal processor may determine how far the membrane 22 has deformed in response to the expansion of the surface 9 of the scalp 8 above the fibrous connective tissue. An illustrative optical sensor system is the optical sensor system employed in optical computer cursor control devices, such as an optical mouse.

In still further embodiments, the movement detector 24 may employ other types of optical sensing technologies. The movement detector 24 may comprise a light emitter 58, a reflective surface 60 on the membrane 22, and an array of photo sensors 62 mounted on the support 20 (or other suitable structure). The reflective surface 60 may be employed on the inward side or surface 38 of the membrane 22 for reflecting light from the light emitter 58 to the array of photo sensors 62 (see FIG. 10). The reflective surface 60 may be provided by a reflective coating or a reflective plate positioned on the inward surface 38 of the membrane 22. The light emitter 58 may direct a beam of coherent light at the reflective surface 60 on the membrane 22, and the beam of light may be reflected onto at least one photo sensor of the array of photo sensors 62 so that movement or deformation of the membrane 22 redirects the light beam from one photo sensor to another photo sensor in the array of photo sensors 62. In some embodiments, a data look-up table may be employed that contains angles associated with the locations of different photo sensors 62 of the array receiving the light beam, and the extent or degree of the deformation of the membrane caused by the movement of the scalp 8 can be calculated by the degree to which the reflected light moves between photo sensors.

In some embodiments, the system 10 includes a signal processing apparatus 14 that is configured to receive the movement signal from the movement detection apparatus 12, and more specifically the movement detector 24. While in some of the most preferred embodiments the signal processing apparatus 14 is connected to the movement detector 24 by wires, other embodiments may implement wireless communication between the apparatus 14 and the detector 24.

The signal processing apparatus 14 may be configured to output signals for different purposes. Primarily, the signal processing apparatus 14 may be operative to process the movement signal into an output signal that is suitable for communicating to other elements of the system 10. In some embodiments, the signal processing apparatus 14 is configured to produce an output signal permitting the data of the movement signal to be displayed on a display screen, and in some embodiments the signal processing apparatus is configured to produce an output signal permitting the data of the movement signal to be depicted by a plotter-type device. The signal processing apparatus 14 may also be configured to direct output to a data recordation or storage device 18.

In greater detail, the signal processing apparatus 14 may translate the output from the movement detector 24 into a data format that is appropriate for communicating with other elements of the detection system 10. Illustratively, the signal processing apparatus 14 may include a microprocessor or other programmed logic that is capable of converting the movement signal to a form suitable for reception by the other elements. The processing apparatus 14 may include communications circuitry and implementing software for formatting the data according to various communication protocols. It should be noted that the inclusion of a microprocessor in the signal processing apparatus 14 may also provide other functions for the system 10 that are not necessarily directly related to the processing of the movement signal (such as functioning as a real time clock for indicating the time duration and time of readings taken, and the like).

Optionally, the signal processing apparatus 14 may also include a communication interface 66 to provide a means for communicating data from the craniosynostosis detection system 10 over a communications network, such as POTS network or the Internet.

In various embodiments, the craniosynostosis detection system 10 includes the data display apparatus 16 configured to display a representation of movement detected by the movement detection apparatus 12, such as visual indicia demonstrating the output of the movement detector 24. The visual indicia may comprise, for example, a line that varies position with time and magnitude of the output of the movement detector 24, or may comprise a bar graph or other form of visual depiction of data over a time period. The data display apparatus 16 may also display other information to the user that is not directly related to the variation of the movement signal over a time period. Such information may include information regarding the identity and condition of the patient, operating status of the system 10 and its components, and the like.

Figure 1:
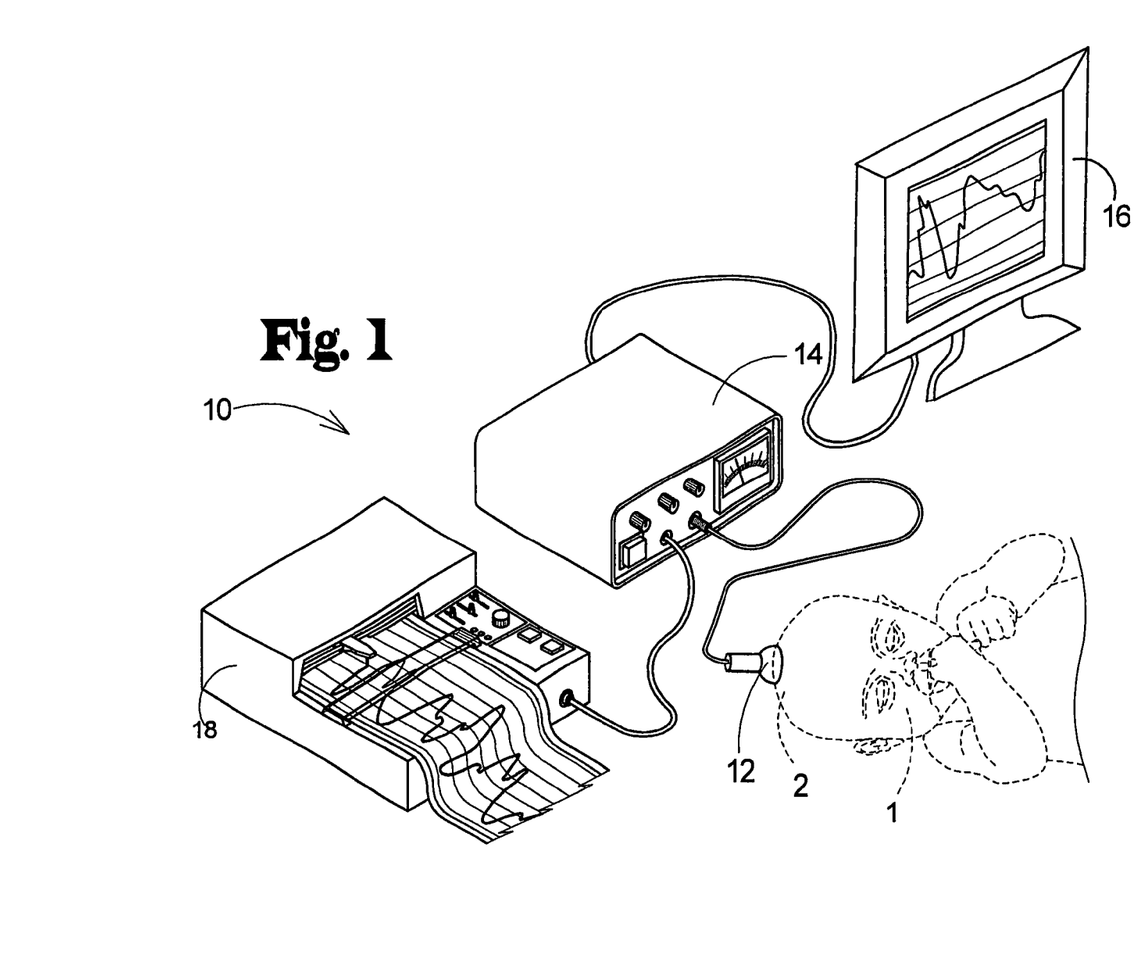
FIG. 1 is a schematic perspective view of various elements of a new craniosynostosis detection system according to the present disclosure.
Figure 2:
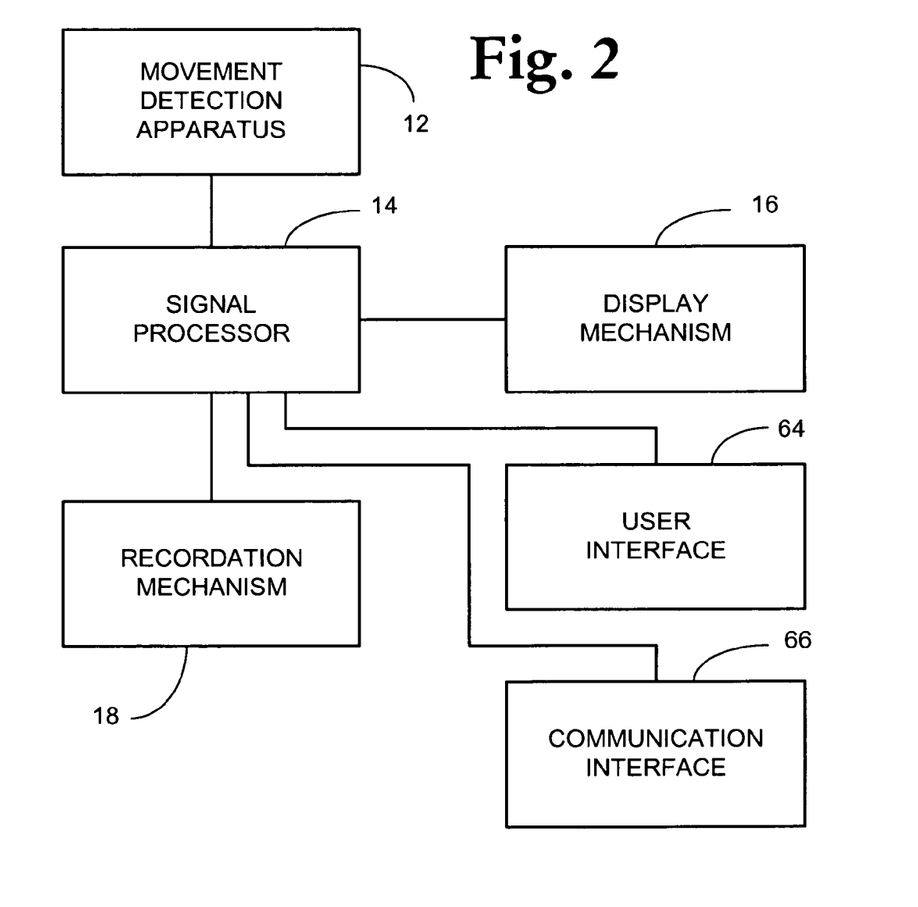
FIG. 2 is a schematic diagrammatic depiction of the detection system, according to an illustrative embodiment.

One embodiment of the data display apparatus 16 is depicted in FIG. 1 depicts the data display apparatus 16 as a display screen, and in this case, as a flat panel display device. The data display apparatus 16 may be a device dedicated to the display of data from the movement detection apparatus 12, but may also be shared with, or dedicated to, another function or apparatus, such as a different medical apparatus or even a personal digital assistant (PDA). Those skilled in the art will recognize that the data display apparatus 16 may take other forms other than a flat screen display, such as a CRT (cathode ray tube) display device, a computer monitor, a laptop computer display, or even a projection display.

The craniosynostosis detection system 10 may further include a data recordation apparatus 18 that is configured to record a representation of movement detected by the movement detection apparatus 12. The data recordation apparatus 18 may create a record of the movement signal from the movement detector 24 (and in some embodiments processed by the signal processing apparatus 14) so that the data can be referenced at a later time. In some embodiments of the system 10, the data recordation apparatus 18 may comprise a plotting or printing device marking a representation of the signal on plotter paper, as shown in FIG. 1, which also serves to display a representation of the movement signal that may be referenced by the user in real time, or as the examination is being conducted. In other embodiments, the data recordation apparatus 18 may comprise digital storage, such as through optical or magnetic means. Thus, the data from the examination may be recorded on a hard disk drive, an optical disk, a memory chip, magnetic tape, and the like. Many means of data storage and retrieval are know to those skilled in the art and could be employed without departing from the scope of the present invention. The data storage apparatus may be integrated with the craniosynostosis detection system 10 or may be separate of the craniosynostosis detection system 10.

In most applications of the invention, the determination of the existence of the craniosynostosis condition in a particular patient is left to the clinician and his or her training and experience in observing and interpreting the indications of movement rendered on, for example, the data display apparatus 16. For example, trained personnel can interpret the output and determine if the movement indicated on the display apparatus 16 corresponds to a pulsing force strong enough to suggest that the bones 4 have not fused and thus the craniosynostosis condition does not exist, or that the movements corresponding to the pulsations are so faint or non-existent to suggest that fusion between the bones 4 is probable and further testing to determine the actual status of the sutures 5 in relation to the ossified bones 4 is warranted.

However, in some applications, the interpretation of the movement signal may be automated and subjected to various algorithms that provide an indication of the fused or non-fused condition of the sutures of the skull of the patient. For example, pattern recognition software may be implemented on the signal processing apparatus 14 (such as on a microprocessor) to signal patterns in the movement signal that might suggest ossification of the sutures 5.

The system 10 may further include an interface 64 configured to receive data input from a user of the system. The user interface 64 may include a keypad, keyboard, and the like.

With respect to the above description then, it is to be realized that the optimum dimensional relationships for the parts of the invention, to include variations in size, materials, shape, form, function and manner of operation, assembly and use, are deemed readily apparent and obvious to one skilled in the art in light of the foregoing disclosure, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the disclosed subject matter to the exact construction and operation shown and described, and accordingly, all suitable modifications and equivalents may be resorted to that fall within the scope of the claims.

I claim:

1. A system for detecting cranial bone movements useful in the diagnosis of craniostenosis, the system comprising:
   a movement detection apparatus configured to detect movement in a surface of the scalp of a patient along areas between bones of the skull when at least a portion of the movement detection apparatus is positioned adjacent to the surface of the scalp, the movement detection apparatus being capable of generating a signal corresponding to movement detected by the movement detection apparatus;
   a signal processing apparatus operatively connected to the movement detection apparatus and configured to receive the movement signal from the movement detection apparatus; and
   a data display apparatus operatively connected to the signal processing apparatus and configured to display a representation of movement detected by the movement detection apparatus;
   wherein the movement detection apparatus comprises a support for positioning adjacent to the scalp of the patient and a flexible membrane mounted on the support such that an outward surface is exposed to directly contact the surface of the scalp to facilitate transmission of movement of the surface of the scalp to the membrane;
   wherein the movement detection apparatus is configured to be held by a hand of a user to maintain contact between the outward surface of the membrane of the movement detection apparatus and the surface of the scalp; and
   wherein the support comprises at least two substantially rigid support portions, the at least two support portions having free ends forming mounting points for the membrane for resting against portions of the patient's scalp located over the bones of the skull, the mounting points being spaced from each other to form a gap of fixed width across which the membrane is suspended free of the support to permit free movement of the membrane with a portion of the patient's scalp over an area between the bones of the skull.

2. The system of claim 1 additionally comprising a data recordation apparatus operatively connected to the signal processing apparatus and configured to record the representation of movement detected by the movement detection apparatus.

3. The system of claim 1 wherein the movement detection apparatus comprises a movement detector in communication with the membrane and configured to detect movement of the membrane, the movement detector being capable of generating the signal corresponding to movement detected by the movement detection apparatus.

4. The system of claim 3 wherein the movement detector is mounted on the membrane to detect movement of the membrane.

5. The system of claim 3 wherein the movement detector is mounted on the support and detects movement of the membrane with respect to the support.

6. The system of claim 3 wherein the movement detector comprises a strain detector device configured to detect strain in the membrane.

7. The system of claim 6 wherein the strain detector device comprises a strain gauge device mounted on an inward surface of the membrane in a manner permitting the strain gauge device to monitor strain in the membrane.

8. The system of claim 7 wherein the movement detection apparatus includes a Wheatstone bridge circuit connected to the strain gauge device to receive strain readings from the strain gauge.

9. The system of claim 1 wherein the membrane is elastomeric.

10. The system of claim 1 wherein the data display apparatus comprises a display screen.

11. The system of claim 1 wherein the data display apparatus comprises a printer.

12. The system of claim 1 additionally comprising a data recordation apparatus operatively connected to the signal processing apparatus and configured to record the representation of movement detected by the movement detection apparatus;
wherein the movement detection apparatus comprises a movement detector mounted on the membrane and configured to detect movement of the membrane with respect to the support and generate the signal corresponding to the detected movement;
wherein the movement detector comprises a strain detector device configured to detect strain in the membrane, the strain detector device comprising a strain gauge device mounted on the membrane in a manner permitting the strain gauge device to monitor strain in the membrane; and
wherein the data display apparatus comprises a display screen.

13. The system of claim 1 wherein the movement detection apparatus comprises a movement detector mounted on the membrane and configured to detect movement of the membrane with respect to the support and generate the signal corresponding to the detected movement.

14. The system of claim 1 wherein the support is substantially U-shaped.

15. A method for detecting cranial bone movements useful in the diagnosis of craniosynostosis in a patient, comprising:
providing a craniosynostosis detection system comprising a movement detection apparatus capable of generating a signal corresponding to movement of an outer surface of a scalp detected by the movement detection apparatus, the movement detection apparatus having a support for positioning adjacent to the scalp of the patient and a membrane with an exposed outward surface positionable over bones of the skull of the patient, the support comprising at least two substantially rigid support portions with free ends forming mounting points for the membrane, the mounting points being spaced from each other to form a gap of fixed width across which the membrane extends free of the support;
holding at least a portion of the outward surface of the membrane in contact with the outer surface of the scalp of the patient, wherein said holding of said at least a portion of the membrane in contact with the surface of the scalp includes resting the mounting points for the membrane against portions of the patient's scalp located over the bones of the skull and contacting the outward surface of the membrane with a portion of the patient's scalp over an area between the bones of the skull; and
detecting a degree of movement of the surface of the scalp of the patient using said at least a portion of the membrane while said at least a portion is held in contact with the outer surface of the scalp by a hand of a user, the movement detection apparatus being capable of generating a signal corresponding to movement of the outer surface of the scalp detected by the movement detection apparatus.

16. The method of claim 14 further including comparing any detected movement of the scalp with a threshold level of movement to determine existence of craniosynostosis.

17. The method of claim 15 wherein detecting comprises measuring strain in the membrane positioned against the surface of the scalp that is caused by movement of the scalp.

18. A system for detecting cranial bone movements useful in the diagnosis of craniosynostosis, the system comprising:
a movement detection apparatus configured to detect movement in a surface of the scalp of a patient along areas between bones of the skull when at least a portion of the movement detection apparatus is positioned adjacent to the surface of the scalp, the movement detection apparatus being capable of generating a signal corresponding to movement detected by the movement detection apparatus;
a signal processing apparatus operatively connected to the movement detection apparatus and configured to receive the movement signal from the movement detection apparatus; and
a data display apparatus operatively connected to the signal processing apparatus and configured to display a representation of movement detected by the movement detection apparatus;
wherein the movement detection apparatus comprises:
a support for positioning adjacent to the scalp of the patient and a flexible membrane, the membrane being mounted on the support such that an outward surface is configured to directly contact the surface of the scalp to facilitate transmission of movement of the surface of the scalp to the membrane, the support comprising at least two substantially rigid support portions, the at least two support portions having free ends forming mounting points for the membrane for resting against portions of the patient's scalp located over the bones of the skull, the mounting points being spaced from each other to form a gap of fixed width across which the membrane is suspended free of the support to permit free movement of the membrane with a portion of the patient's scalp over an area between the bones of the skull; and
a movement detector mounted on the membrane and configured to detect movement of the membrane with respect to the support and configured to generate the signal corresponding to the detected movement.

* * * * *